(12) United States Patent
Scherer et al.

(10) Patent No.: US 8,787,752 B2
(45) Date of Patent: Jul. 22, 2014

(54) SYSTEMS AND METHODS FOR OPTICALLY POWERING TRANSDUCERS AND RELATED TRANSDUCERS

(75) Inventors: Axel Scherer, Laguna Beach, CA (US); Aditya Rajagopal, Irvine, CA (US); Seheon Kim, Pasadena, CA (US); Andrew P. Homyk, South Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 427 days.

(21) Appl. No.: 12/860,723

(22) Filed: Aug. 20, 2010

(65) Prior Publication Data
US 2011/0044694 A1    Feb. 24, 2011

Related U.S. Application Data

(60) Provisional application No. 61/236,024, filed on Aug. 21, 2009.

(51) Int. Cl.
*H04B 10/08* (2011.01)

(52) U.S. Cl.
USPC .............. 398/22; 398/9; 398/115; 398/118; 398/130; 356/300; 356/302; 356/317

(58) Field of Classification Search
USPC ......... 398/171, 151, 140, 118, 116, 117, 115, 398/38, 9, 25, 33, 106, 109, 108, 182, 22, 398/128, 130, 135, 138, 141, 172; 356/300, 356/301, 302, 317, 319, 320; 250/214.1, 250/227.11, 338.1, 341.1; 438/24; 257/E31.095
See application file for complete search history.

(56) References Cited

U.S. PATENT DOCUMENTS

| | | | |
|---|---|---|---|
| 4,825,081 A | | 4/1989 | Wille |
| 5,545,980 A | * | 8/1996 | Nakamoto ............... 324/96 |
| 6,255,976 B1 | * | 7/2001 | Watanabe et al. ........ 341/143 |
| 6,437,554 B1 | | 8/2002 | Atwater |
| 6,754,950 B2 | | 6/2004 | Furukawa et al. |
| 6,963,119 B2 | | 11/2005 | Colgan et al. |
| 7,598,552 B2 | | 10/2009 | Park |
| 2003/0090161 A1 | * | 5/2003 | Marlow et al. ........... 307/149 |
| 2003/0099273 A1 | * | 5/2003 | Murry et al. ............ 372/108 |
| 2007/0116082 A1 | | 5/2007 | Feve |

(Continued)

FOREIGN PATENT DOCUMENTS

| | | |
|---|---|---|
| JP | 05-243588 | 9/1993 |
| JP | 2001-250967 | 9/2001 |

(Continued)

OTHER PUBLICATIONS

PCT International Search Report issued for PCT/US2010/046220 filed Aug. 20, 2010 in the name California Institute of Technology et al.

(Continued)

*Primary Examiner* — M. R. Sedighian
(74) *Attorney, Agent, or Firm* — Steinfl & Bruno LLP

(57) ABSTRACT

The present disclosure describes an optically powered transducer with a photovoltaic collector. An optical fiber power delivery method and system and a free space power delivery method are also provided. A fabrication process for making an optically powered transducer is further described, together with an implantable transducer system based on optical power delivery.

18 Claims, 11 Drawing Sheets

(56) References Cited

U.S. PATENT DOCUMENTS

| | | | |
|---|---|---|---|
| 2007/0187632 A1 | 8/2007 | Igarashi | |
| 2008/0039770 A1* | 2/2008 | Francis et al. | 604/20 |
| 2008/0089367 A1 | 4/2008 | Srinivasan | |
| 2009/0015141 A1* | 1/2009 | Wang et al. | 313/504 |
| 2010/0084729 A1 | 4/2010 | Steinbrueck | |
| 2011/0044694 A1 | 2/2011 | Scherer et al. | |

FOREIGN PATENT DOCUMENTS

| | | |
|---|---|---|
| JP | 2004-363594 | 12/2004 |
| JP | 2006-266846 | 10/2006 |
| JP | 2006-267477 | 10/2006 |
| KR | 10-1999-0028493 | 4/1999 |
| KR | 10-0781545 | 12/2007 |
| KR | 10-0906270 | 7/2009 |

OTHER PUBLICATIONS

PCT Written Opinion issued for PCT/US2010/046220 filed Aug. 20, 2010 in the name California Institute of Technology et al.

Andre, W., et al., Micro-photovoltaic Cells Designed for Magnetotaxis-based Controlled Bacterial Microrobots, IEICE Electronics Express, 2008, 5: 101-106.

PCT International Search Report mailed on May 16, 2013 issued for PCT/US2013/025632 filed Feb. 11, 2013 in the name of California Institute of Technology.

PCT Written Opinion mailed on May 16, 2013 issued for PCT/US2013/025632 filed Feb. 11, 2013 in the name of California Institute of Technology.

Fujita, M., et al., *Continuous wave lasing in GaInAsP microdisk injection laser with threshold current of 40 µA*, Electron. Lett., 2000, vol. 36, pp. 790-791.

Mo, Y. et al., *Micro-machined gas sensor array based on metal film micro-heater*, Sensors and Actuators B, 2001, vol. 79, pp. 175-181.

Ushigome, R. et al., *GaInAsP microdisk injection laser with benzocyclobutene polymer cladding and its athermal effect*, Jpn. J. Appl. Phys., 2002, vol. 41, pp. 6364-6369.

Inoshita, K. et al., *Fabrication of GaInAsP/InP photonic crystal lasers by ICP etching and control of resonant mode in point and line composite defects*, IEEE J. Sel. Top. Quantum Electron, 2003, vol. 9, pp. 1347-1354.

Sadek, A.S. et al., *Wiring nanoscale biosensors with piezoelectric nanomechanical resonators*, Nano Lett., 2010, vol. 10, pp. 1769-1773.

Restriction Requirement mailed on Sep. 20, 2013 issued for U.S. Appl. No. 13/764,620, filed Feb. 11, 2013 in the name of Seheon Kim.

* cited by examiner

SYSTEMS AND METHODS FOR OPTICALLY POWERING TRANSDUCERS AND RELATED TRANSDUCERS

CROSS REFERENCE TO RELATED APPLICATIONS

The present application claims priority to U.S. Provisional Application No. 61/236,024, filed on Aug. 21, 2009, which is incorporated herein by reference in its entirety.

STATEMENT OF GOVERNMENT GRANT

The U.S. Government has certain rights in this invention pursuant to Grant No. HR0011-04-1-0054 awarded by DARPA.

FIELD

The present disclosure relates to transducers. More particularly, the present disclosure relates to systems and method for optically powering transducers and related transducers.

SUMMARY

According to a first aspect, an optically powered transducer is provided, comprising: a sensor circuitry adapted to convert an environmental or ambient signal of interest into a sensor electrical signal; an electronic circuitry adapted to process the sensor electrical signal; and a photovoltaic collector adapted to collect optical energy, convert the optical energy to electrical energy and power the sensor circuitry and the electronic circuitry with the electrical energy.

According to a second aspect, a method for fabricating an optically powered transducer is provided, comprising: fabricating a sensor circuitry and an electronic circuitry on a transducer substrate, said transducer substrate being on top of a sacrificial layer; fabricating a photovoltaic collector on the transducer substrate, the photovoltaic collector adapted to adapted to collect optical energy, convert the optical energy to electrical energy and power the sensor circuitry and the electronic circuitry with the electrical energy; providing a communication light source on the transducer substrate; and releasing the sacrificial layer.

According to a third aspect, a fiber optic power delivery system is provided, comprising at least one monitoring system; at least one optical fiber; and at least one transducer adapted to be optically powered by the at least one monitoring system through the at least one optical fiber.

According to a fourth aspect, a method for optically powering a transducer is provided, comprising directing optical energy at the transducer through an optical fiber.

According to a fifth aspect, a method for powering an optically powered transducer is provided, comprising directing optical energy at the optically powered transducer in absence of an optical fiber arrangement.

According to a sixth aspect, a method for exchanging information with at least one optically powered transducer is provided, comprising: powering the at least one optically powered transducer by directing optical energy at the optically powered transducer; establishing a wireless data link with each of the at least one optically powered transducers; and exchanging information with each of the at least one optically powered transducers through the wireless data link.

Further embodiments of the disclosure are provided in the specification, drawings and figures of the present application.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Throughout the specification, the term "photovoltaic collector" refers to a device/component/apparatus that collects optical energy and convert the optical energy to electrical energy. For example, a photovoltaic collector may be a silicon-based P-N junction. A person having ordinary skill in the art would understand that a photovoltaic collector may be fabricated with other materials and the material for a photovoltaic collector may be selected to achieve different target conversion efficiencies in different situations.

Figure 1:
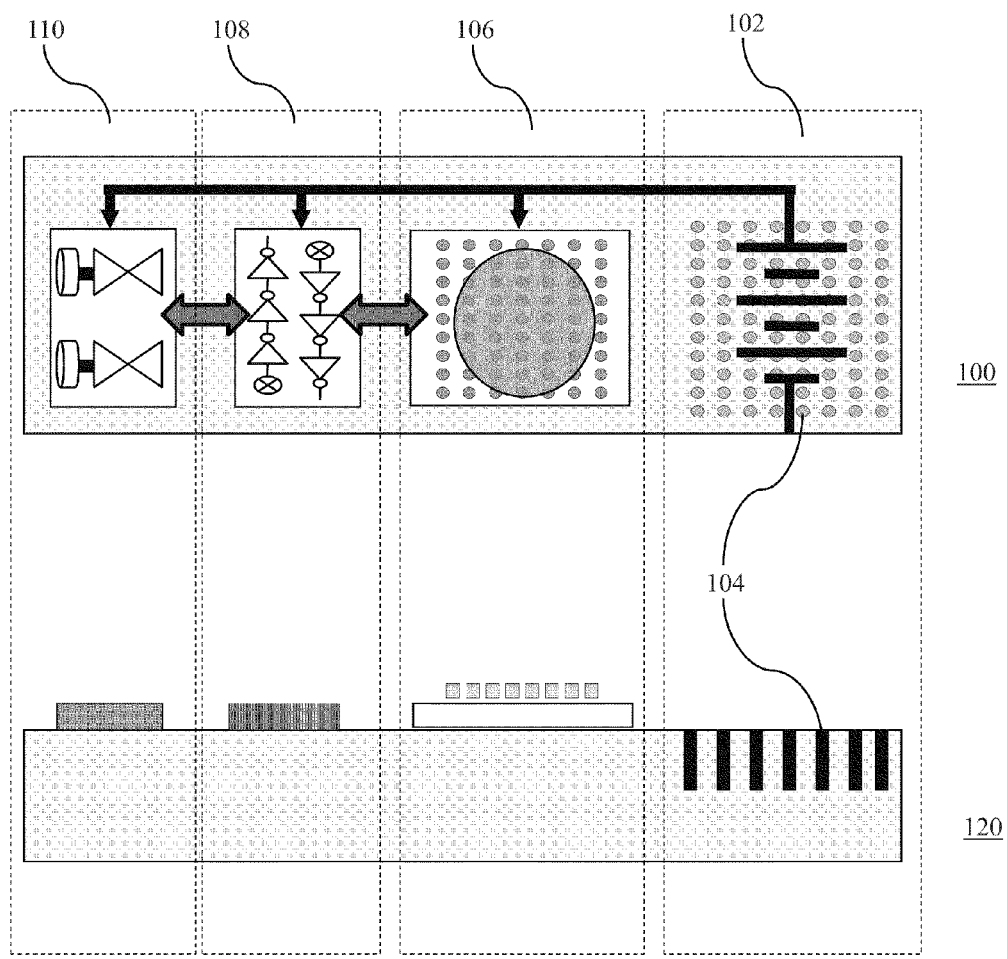
FIG. 1 shows a top view and a cross-section view of an optically powered transducer, in accordance with an embodiment of the present disclosure.

FIG. 1 shows a top view (100) and a cross-sectional view (120) of an optically powered transducer, in accordance with an embodiment of the present disclosure. In this embodiment, the optically powered transducer is powered by optical energy. With sufficient power, the optically powered transducer measures or picks up signals of environmental interest (e.g., blood sugar concentration, and neuron electric potential). The optically powered transducer then transmits data that is indicative of the signals of interest wirelessly. The signal transmission may be optical or other electromagnetic waves (e.g., WiFi, and Bluetooth®).

With continued reference to FIG. 1, the optically powered transducer comprises a photovoltaic collector (102), an electronic circuitry (108), and a sensor circuitry (110). According to a further embodiment of the present disclosure, the optically powered transducer further comprises a communication light source (106) that may transmit optical data indicative of the signals of interest (e.g., blood sugar concentration). In a still further embodiment, the communication light source (106) may comprise a laser, or a light-emitting diode.

The photovoltaic collector (102) collects optical energy, converts the optical energy into electrical energy and powers the electronic circuitry (108), the communication light source (106), and the sensor circuitry (110). In another embodiment of the communication light source may directly collect optical energy and powers itself. The sensor circuitry (110) measures or picks up environmental signals of interest, such as pressures, light, temperatures, RF electromagnetic waves, etc and converts signals of interest into electrical signals. The electronic circuitry (108) processes the signals from the sensor circuitry (110) and drives the communication light source (106) to transmit light signals indicative of the environmental signals of interest picked up by the sensor circuitry (110).

Figure 2:
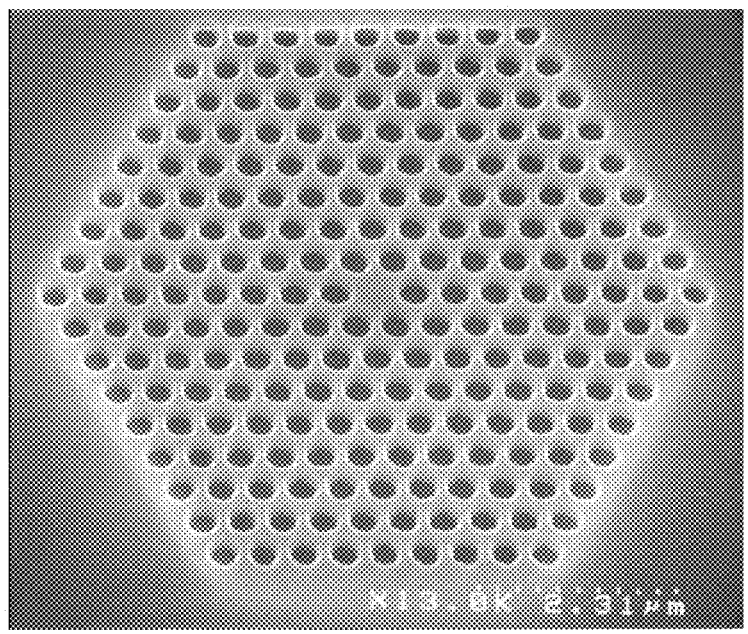
FIG. 2 shows micro-fabricated resonant cavities, suitable for the transducers of FIG. 1.

According to an embodiment of the present disclosure, the photovoltaic collector (102) collects optical energy and powers the optically powered transducer. By way of example, the photovoltaic collector (102) comprises resonant cavities (104) and one or more photovoltaic junctions. The resonant cavities are located surrounding the photovoltaic junctions. According to a further example, the resonant cavities (104) comprise high finesse cavities. The resonant cavities (104) may increase the effective photon path length and photon absorption efficiency of the photovoltaic junctions. In addition, the resonant cavities (104) or other surface gratings may divert incoming light vertically incident to the photovoltaic slab (the material that absorbs light and converts it into electric current) into the in-plane direction (the direction parallel to the original wafer surface). According to another embodiment of the present disclosure, a photovoltaic collector with resonant cavities has a smaller size than one with no resonant cavity. FIG. 2 shows micro-fabricated resonant cavities, in accordance with an embodiment of the present disclosure. According to a further embodiment, vertical cavities can be provided to increase the collection efficiency. Such cavities are typically called Fabry-Perot resonators with dielectric or metallic minors deposited on top and bottom of the p-n junction.

According to an embodiment of the present disclosure, the short circuit current density in a monochromatic (laser illuminated) photovoltaic collector is $$J_{SC} = q \cdot N \cdot QE, \quad (1)$$

where q is electronic charge, N is density of incident photons (q·N is the incident charge density/photon energy) and QE is (external) quantum efficiency. In theory, maximum available output power density can be given by product of the maximum output voltage (open circuit voltage, $V_{OC}$), and the maximum available current density (short circuit current density, $J_{SC}$). However, in practice, it is not possible to obtain that maximum power because of loading effects. Usually, a fill factor is defined to illustrate the effect of the load on the cell. The fill factor can be described by the following equation:

$$FF = \frac{J_{MX} \cdot V_M}{J_{SCX} \cdot V_{OC}}. \quad (2)$$

where $J_M$ and $V_M$ are the current density and the output voltage at the maximum power point. Therefore, the maximum output power density would be $$P_M = V_{MX} \cdot J_M. \quad (3)$$

$P_M$ is often represented in terms of cell characteristics as $$P_M = FF_X \cdot V_{OCX} \cdot J_{SC}, \quad (4)$$

and conversion efficiency can be defined as $$\eta = \frac{P_M}{P_{in}} \cdot 100. \quad (5)$$

By way of example, not of limitation, TABLE 1 shows calculation results of efficiencies and output power for an input power density of 10 mW/cm². Calculations of the Best Case are based on the following assumptions: QE=95%; junction ideality factor n=1; and $J_M$=95% of short circuit current density. In addition, series resistance is approximated as the diode resistance of the cell and shunt resistance is ignored. For the Practical Case, calculations are based on the following assumptions: QE=65%; junction ideality factor n=1.5; transmission coefficient=0.9 (0.9² for power transmission coefficient).

TABLE 1

| | $P_{in}$ (mW/cm²) | $P_{out}$ (mW/cm²) | $P_{in}$ (mW) | $P_{out}$ (mW) | Efficiency |
|---|---|---|---|---|---|
| Best Case | 10 | 4.8 | 0.2 | 0.095 | 48% |
| Practical Case | 10 | 3.1 | 0.2 | 0.061 | 31% |

Best Case: QE = 0.95, n = 1, Rs = rs/A, rs = VT/Jsc, A = 2 mm².
Practical Case: QE = 0.65, n = 1.5, Rs = rs/A, rs = VT/Jsc, A = 2 mm².

Figure 3A:
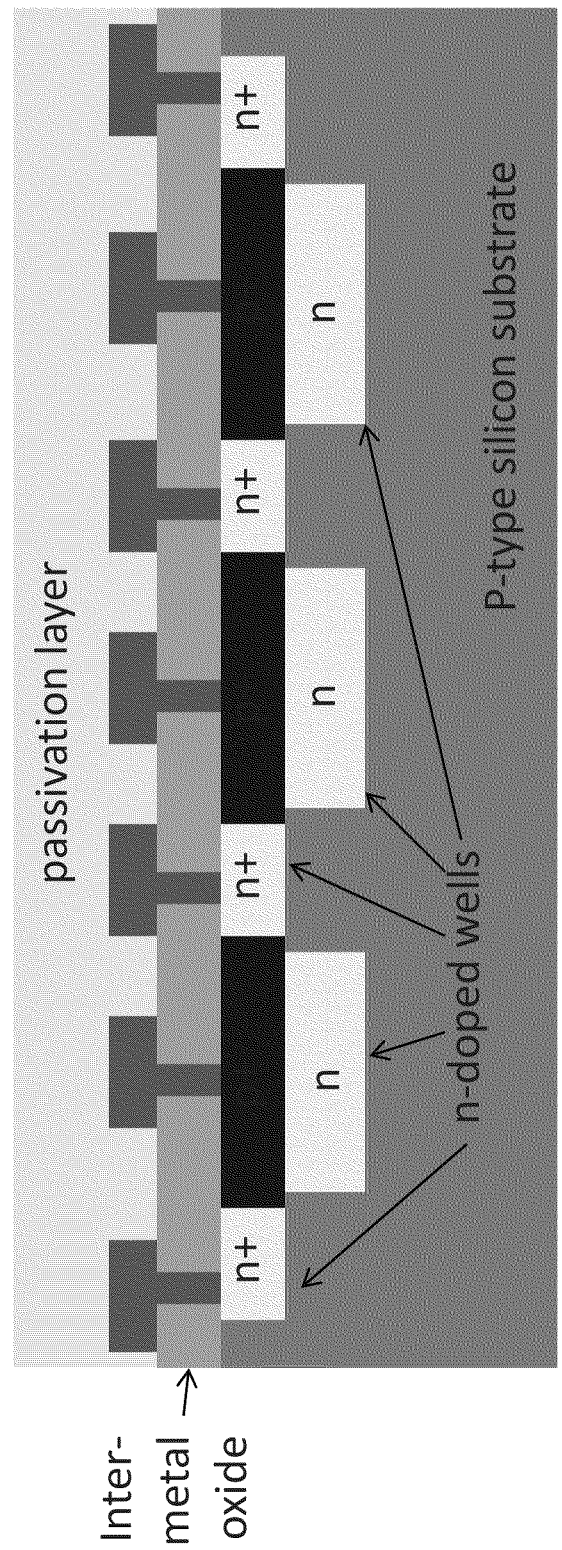
FIGS. 3A-3C show views of a photovoltaic collector suitable to be used with the optically powered transducer in accordance with an embodiment of the present disclosure.
Figure 3B:
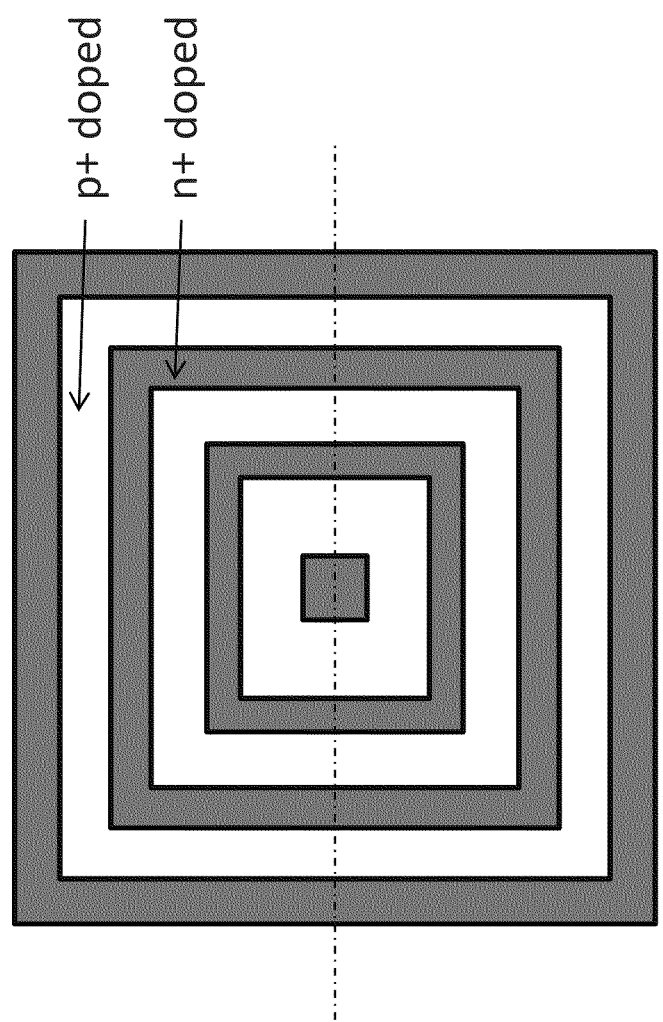
Figure 3C:
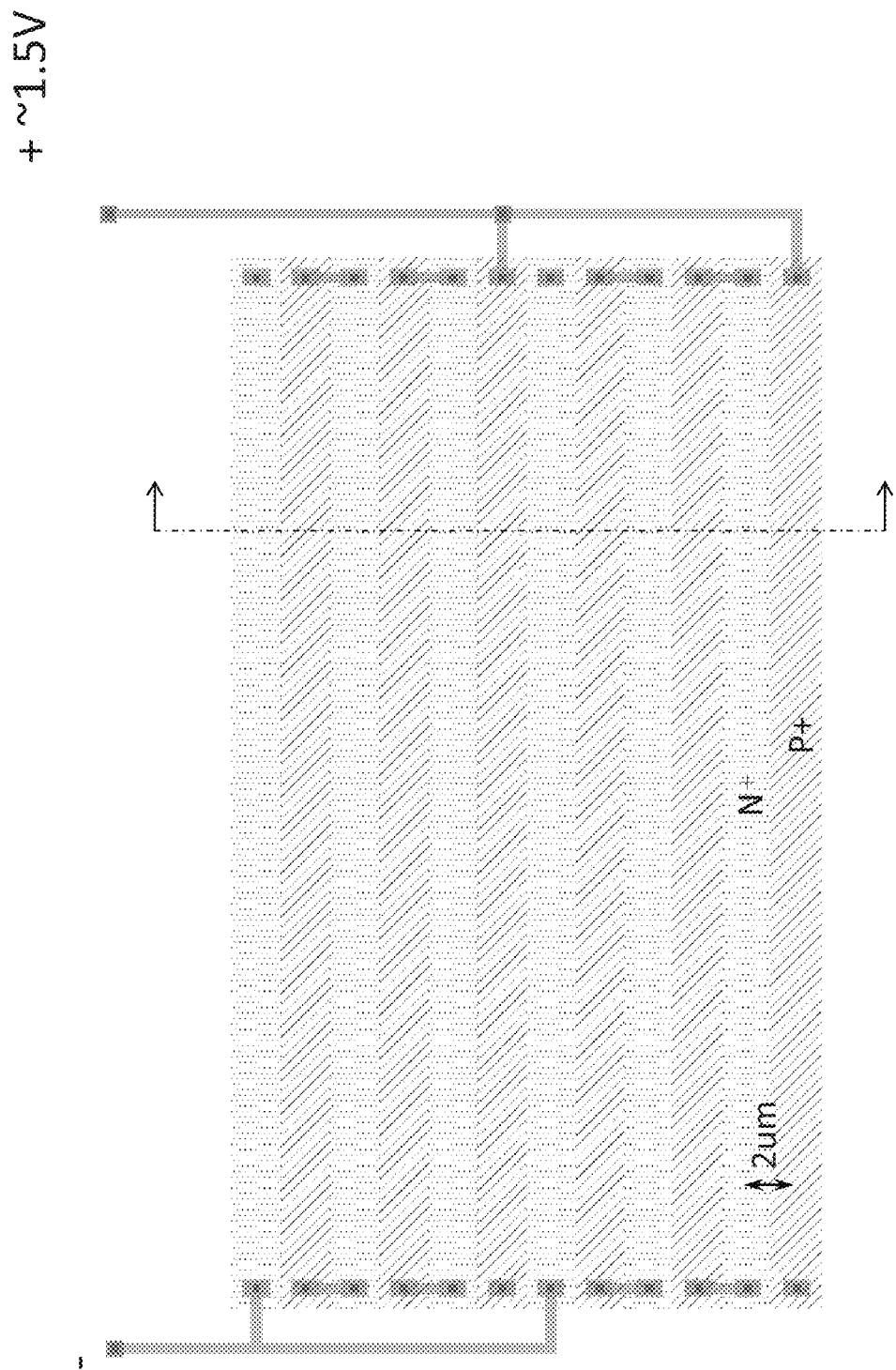

FIGS. 3A-3C show views of a photovoltaic collector suitable to be used with the optically powered transducer in accordance with an embodiment of the present disclosure. The cell of FIG. 3A is a photovoltaic cell constructed by a standard CMOS process in a silicon foundry.

Figure 4:
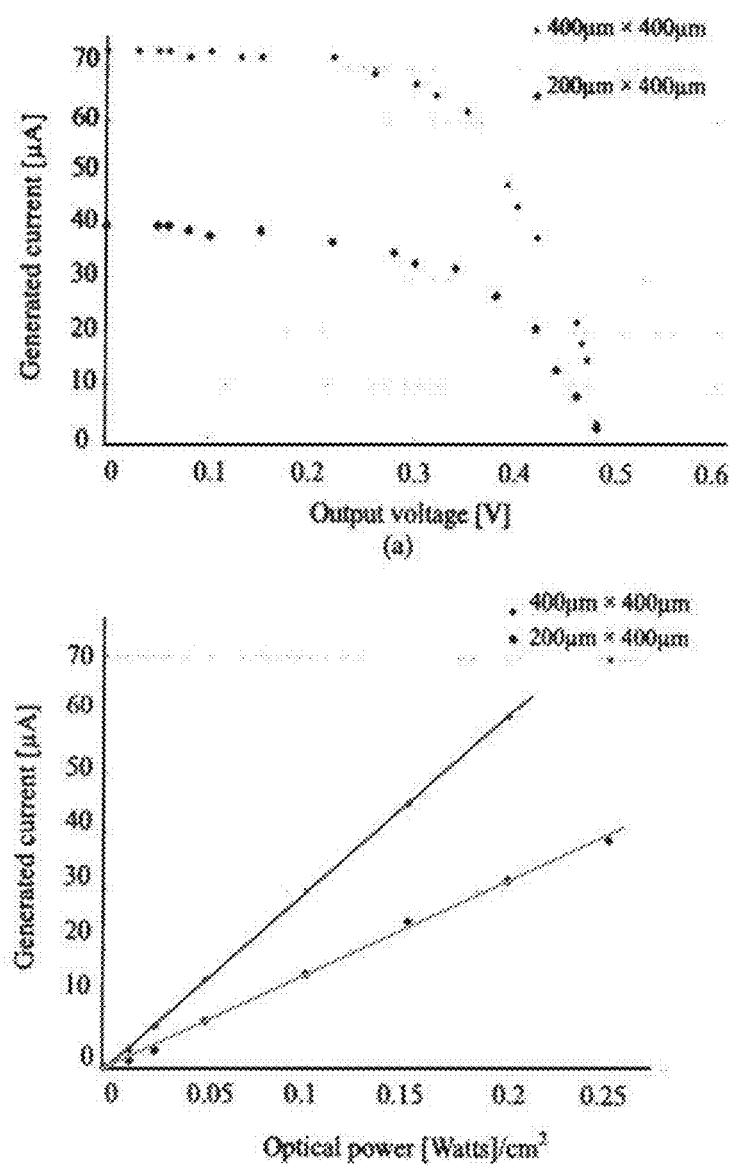
FIG. 4 shows electrical power output versus input optical power diagrams measured from photovoltaic collectors fabricated with CMOS-compatible processes, in accordance with an embodiment of the present disclosure.

FIG. 4 shows electrical power output versus input optical power diagrams measured from photovoltaic collectors fabricated with CMOS-compatible processes. The figure is taken from André W. and Martel S., "Micro-photovoltaic cells designed for magnetotaxis-based controlled bacterial microrobots," IEICE Electronics Express, Vol. 5 (2008), No. 3 pp. 101-106, which is incorporated herein by reference in its entirety. The photovoltaic collectors have very linear current-power relationship. Indeed, the current extracted from the photovoltaic collector is linearly dependent on the incident power of light over a large range of incident power densities, far beyond the ones shown in the case of photovoltaic collectors in FIG. 4 with ~0.25 W/cm². At 0.25 W/cm², 50 µA can be generated from a 400×400 µm photovoltaic collector, and 30 µA is generated in a 200×400 µm photovoltaic collector. In a further embodiment, the photovoltaic collectors can be irradiated with up to 10 kW/cm² (over 4 orders of magnitude above the power levels shown in FIG. 4) before the P-N junction in the photovoltaic collector becomes saturated with carriers and no longer acts as a p-n junction. This implies that the photovoltaic collector can be further reduced in size. Thermal effects may ultimately limit the conversion efficiency of such photovoltaic collectors far before kW/cm² power densities are reached. By pulsing with higher power densities of kW/cm², the area for power generation can be significantly reduced, promising further miniaturization of the optically powered transducer.

By way of example and not of limitation, the sensor circuitry (110) of the optically powered transducer of FIG. 1 may be an implantable pressure sensor, a medical implant, a blood sugar detector, an autonomous sensor, a humidity sensor, a gas sensor, a pathogen sensor, a light sensor, a stress or strain sensor, a motion sensor, etc.

There are several methods for measuring blood sugar optically. The simplest is by observing the change in the refractive index of the serum or plasma. Increased sugar content will increase that refractive index. However, also the amount of water in the body will change the refractive index. Such kind of test could be used for monitoring rapid changes in the blood glucose level. Another way of measuring the blood sugar optically is through absorption spectroscopy, in which the optical incident light excites some vibrational modes of the sugar molecules (dextrose, glucose, etc) and these increase the absorption proportional to the amount of sugar in the blood. A third way to measure the blood sugar is through Raman spectroscopy, in which light at high intensity excites the sugar molecules, and light that is shifted (typically to lower energy) comes out of the illuminated region. That additional light can be measured with a filtered detector and the difference in energy between the emitted light and the pump light can be very specific to the vibrational modes that have been excited in the sugar molecules. Resonant Raman measurements provide the most specific optical measurement of blood glucose.

According to another embodiment of the present disclosure, the electronic circuitry (108) of FIG. 1 may also include a capacitor or other energy storage component. The electrical energy generated from the photovoltaic collector (102) may be stored in the capacitor or other energy storage component. The stored electrical energy may be used to power the sensor circuitry (110) and the electronic circuitry (108). Optionally, the stored electrical energy may be used to drive the communication light source (106).

In a still further embodiment, the electronic circuitry (108) of FIG. 1 comprises a circuitry that controls the communication light source (106) of the optically powered transducer. According to another embodiment of the present disclosure, the electronic circuitry (108) may contain programs or information that defines the transducer's functions and make the transducer wireless.

According to an embodiment of the present disclosure, the electronic circuitry (108) of FIG. 1 processes the output from the sensor circuitry (110). By way of example, not of limitation, the electronic circuitry (108) may comprise CMOS silicon circuits that perform amplification and amplitude-to-pulse-width conversion. With these circuits, the electronic circuitry (108) may amplify the output from the sensor circuitry and modulate the output according to an amplitude-to-pulse-width conversion. The electronic circuitry (108) may also comprise a driving circuitry that drives the communication light source (106). The electronic circuitry (108) can be fabricated in silicon by CMOS processing by using appropriate mask sets, tested while still on the wafer, and subsequently removed from its original substrate.

Figure 5:
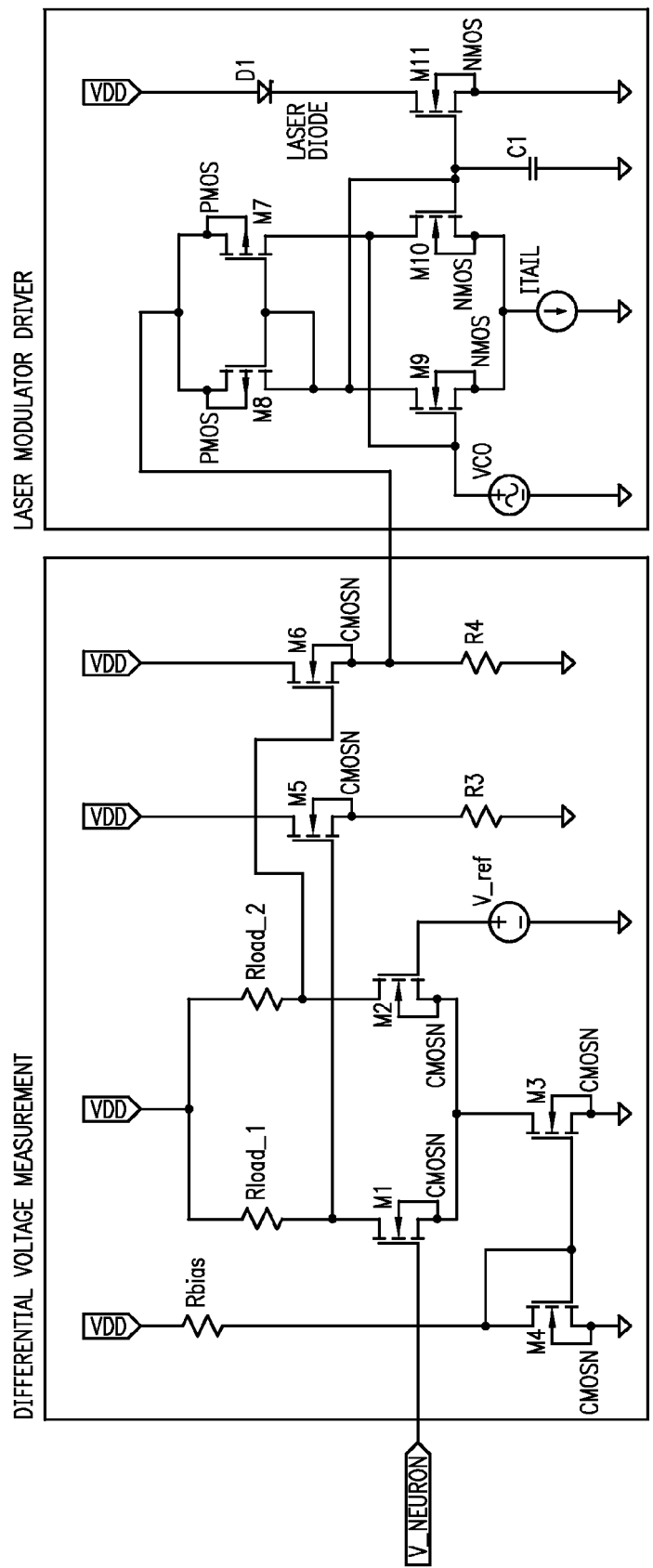
FIG. 5 shows an example of a CMOS laser driving circuit suitable to be used with the optically powered transducer of FIG. 1.

FIG. 5 shows an example of a CMOS laser driving circuit suitable to be used with the optically powered transducer of FIG. 1.

With reference to FIG. 1 again, the communication light source (106) can provide the optically powered transducer with a wireless, optical data link to other devices. The communication light source (106) can be either a light emitting diode or a semiconductor laser. According to a further embodiment, the communication light source (106) may serve as the light source for spectroscopic measurements. For example, a communication laser may also be the light source for refractive index measurements for blood sugar monitoring application.

In particular, the blood sugar measuring examples mentioned above with the refractive index, the absorption and the Raman measurement, may be performed by lasers in the near-infrared, e.g. by changing laser emission wavelength or laser intensity, or by emitting additional wavelengths. Therefore, the same laser that transmits the power to the device or the one that performs the data communications function can also be used to perform the optical spectroscopy test.

The communication light source (106) may be powered by the photovoltaic collector (102). In another embodiment, the communication light source (106) may collect optical energy by itself and powers itself. This can be done by direct optical pumping close to the threshold values of the communication light source).

In particular, the light (incident light in the near-infrared) used to convert into photo-current for the photovoltaic collector can be used for an additional purpose of exciting carriers in the on-chip laser on the autonomous system. These carriers in turn generate light (i.e. photoluminescence) in that laser. That laser starts to emit light at its resonant frequency—i.e. it is an optically pumped laser. At this point, if it is desired to use the laser to transmit information, all what is needed is to turn the laser off rather than on. This is called Q-switching, and can be done electrically. Therefore, such embodiment may be useful in terms of power, as there is no need to supply the power for the on-chip laser from the photovoltaic power generator, as the power can be laser based on photoluminescence with the abundant external light that needs to be there anyway for the photovoltaic generator.

Figure 6:
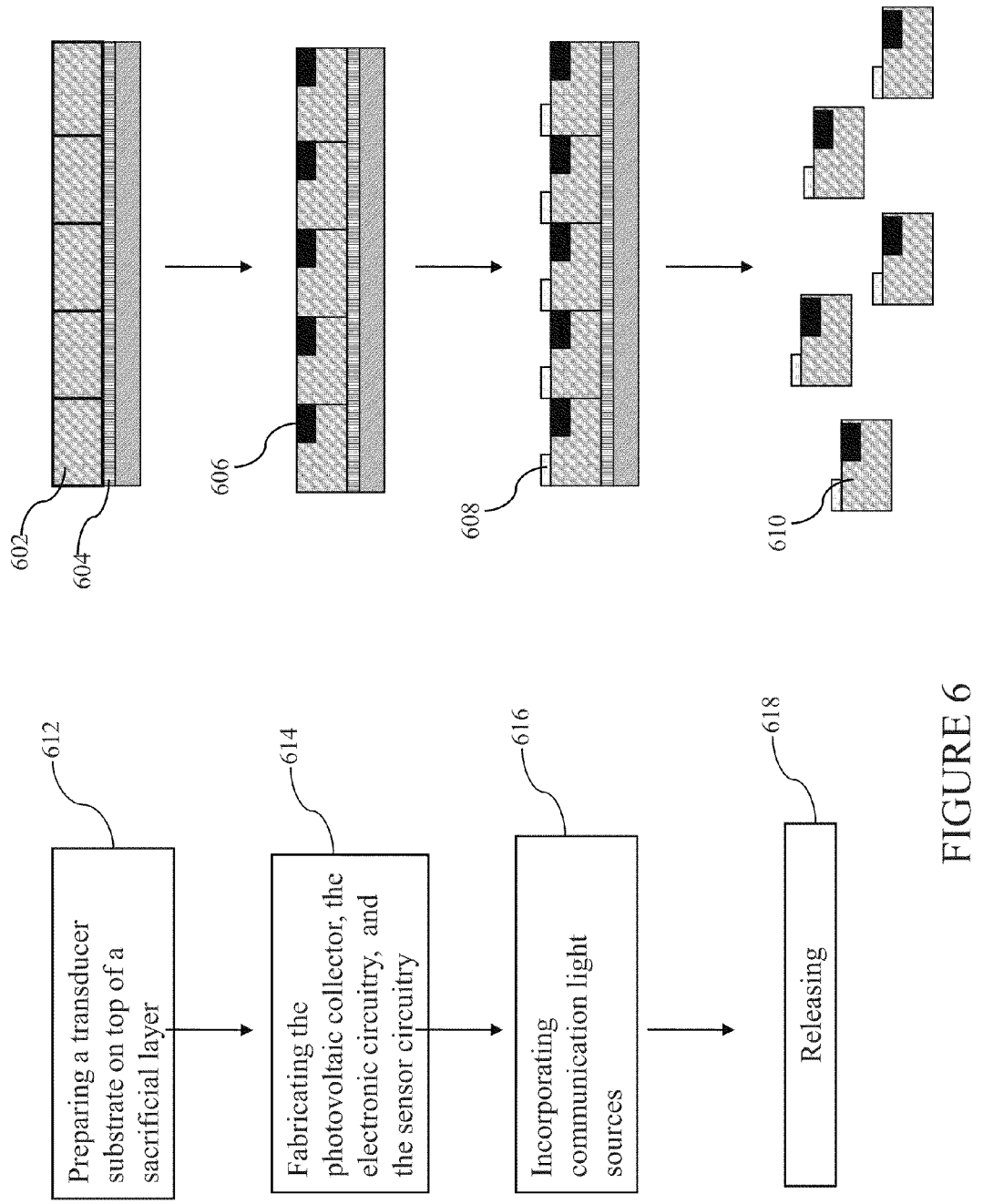
FIG. 6 shows a fabrication process of an optically powered transducer, in accordance with an embodiment of the present disclosure.

FIG. 6 shows a fabrication process of an optically powered transducer, in accordance with an embodiment of the present disclosure. According to this embodiment, the fabrication starts with preparing (612) a transducer substrate (602) on top of a sacrificial layer (604). For example, the transducer substrate (602) and the sacrificial layer (604) are selected to be compatible with silicon-based CMOS processing technologies.

Next, the photovoltaic collector (608), the electronic circuitry, and the sensor circuitry are fabricated (614) on the transducer substrate (602). These components can be fabricated with CMOS-compatible processing technologies.

Next, a communication light source (608) is placed (616) on the transducer substrate (602). For example, the communication light source can be placed by wafer bonding technologies. The optically powered transducer may be tested before the final releasing. Then, the optically powered transducer (610) is released (618). The optically powered transducer (610) has a size ranging from 10 microns to 500 microns.

Fiber-optics provides high-bandwidth communications between devices within optical systems. Many modern platforms are equipped with fiber optic communication systems. Such fiber optic systems are typically optimized for low dispersion and minimal absorption loss operation at bandwidths in excess of several gigabits per second. The bandwidth available within these fiber optic systems is often underutilized, as high frequency fiber communications is optimized for small spectral regions with low-loss wavelength "bands."

Figure 7:
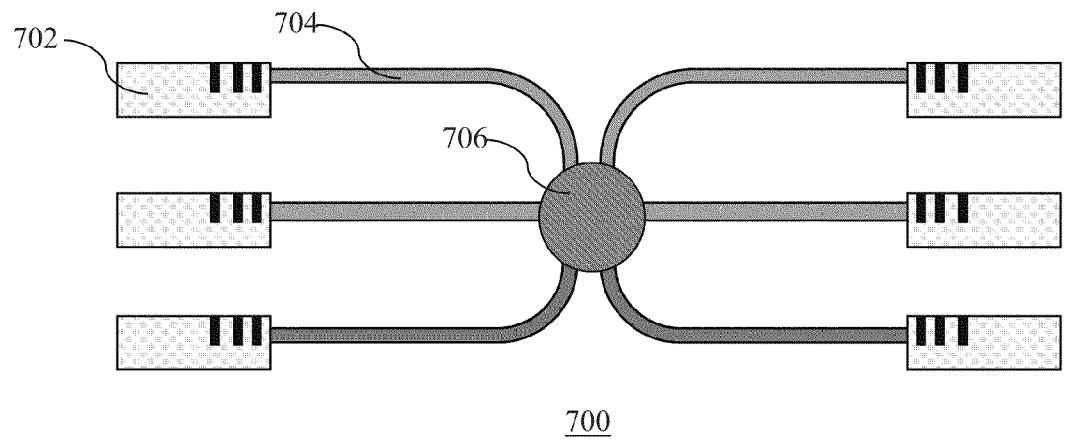
FIG. 7 shows a fiber-based power delivery system for an optically powered transducer, in accordance with an embodiment of the present disclosure.

FIG. 7 shows a fiber-based power delivery system, in accordance with an embodiment of the present disclosure. According to this embodiment, the fiber power delivery system (700) comprises at least one monitoring system (706), at least one optical fiber (704), and at least one optically powered transducer (702). In a further embodiment, the fiber power delivery system (700) distributes power and sensing/monitoring signals through a spectral region different from that used by a high-speed fiber optic communication system.

Examples of such monitoring systems can include a broader version of the same approaches described above in the blood glucose case. If, for example, a chemical with a specific absorption resonance in the atmosphere or in a water sample is to be measured, the chemical can be bound to the surface of a fiber-based detection system, and measured by observing the refractive index (through changes in resonance wavelength of our laser or a cavity), the absorption (through changes in current from our photovoltaic power supply), or through the intensity of the Raman-shifted light (by looking at the spectrum of light coming back through the fiber). By way of example, the same chips that are described as implanted devices can be used, bonded to the end of a fiber, and ambient chemistry rather than blood chemistry can be measured.

The optically powered transducer (702) receives power from the monitoring system (706) through the optical fiber (704). In a further embodiment, the optically powered transducer (702) communicates with the monitoring system at low bit rates. In a further embodiment, the optically powered transducer (702) collects the optical power with a photovoltaic collector. As explained with reference to FIG. 1, the photovoltaic collector of the optically powered transducer (702) may have resonant cavities. Powered by an optical fiber, the optically powered transducer (702) does not need to use extra electrical connections for power delivery. Communicating at lower bit rates may reduce ambient influences (e.g. temperature and humidity) on the optically powered transducer's sensitivity.

According to another embodiment of the present disclosure, the optically powered transducer (702) may compare signals from other parts of the network and reduce false positive alarm rates by looking for a trend to confirm whether the device is working or not.

According to an embodiment of the present disclosure, the fiber power delivery system uses as optical power sources monochromatic high-power pump lasers at 850 nm or 980 nm.

Figure 8:
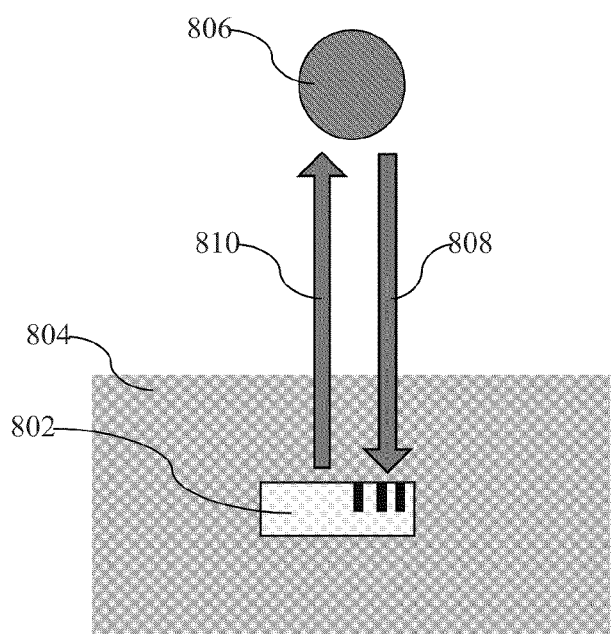
FIG. 8 shows a free space power delivery scheme for an optically powered transducer, in accordance with an embodiment of the present disclosure.

FIG. 8 shows a free space power delivery scheme, in accordance with an embodiment of the present disclosure. In this embodiment, an optically powered transducer (802) is powered by incoming light (808) from a monitoring system (806). No optical fiber is used. According to a further embodiment, the optically powered transducer (802) may transmit information to the monitoring system (806) or other device through outgoing light (810) from the optically powered transducer's optical communication source (e.g. vertical or lateral cavity lasers).

If desired, the optically powered transducer (802) can be placed in a medium (804). The medium (804) may be animal or human body tissues (804). In another embodiment, the optically powered transducer may be placed in other media, such as oil, water, etc. Power delivery and signal transmission would not be obstructed as long as the medium (804) has sufficiently high transmission at the light wavelength the optically powered transducer (802) uses. For example, human body tissues have low absorption at light wavelength longer than 700 nm. Therefore, light with a wavelength of around 850 nm can be used for power delivery and signal transmission.

According to a further embodiment of the present disclosure, the optically powered transducer (802) may comprise the electronic circuitry and/or the sensor circuitry of the optically powered transducer of FIG. 1. As usual, if desired, these circuitries may be fabricated with CMOS-compatible processing technologies.

Because the optically powered transducer is small (e.g., from several millimeters to several microns in lateral dimensions) and because no optical fiber is used, the free space power delivery scheme is useful in medical implant applications or other applications that require small volumes. For example, the free space power delivery scheme may be useful for monitoring fuel tanks, determining mechanical strain in structural elements and free-space communications within systems, like military systems.

Figure 9:
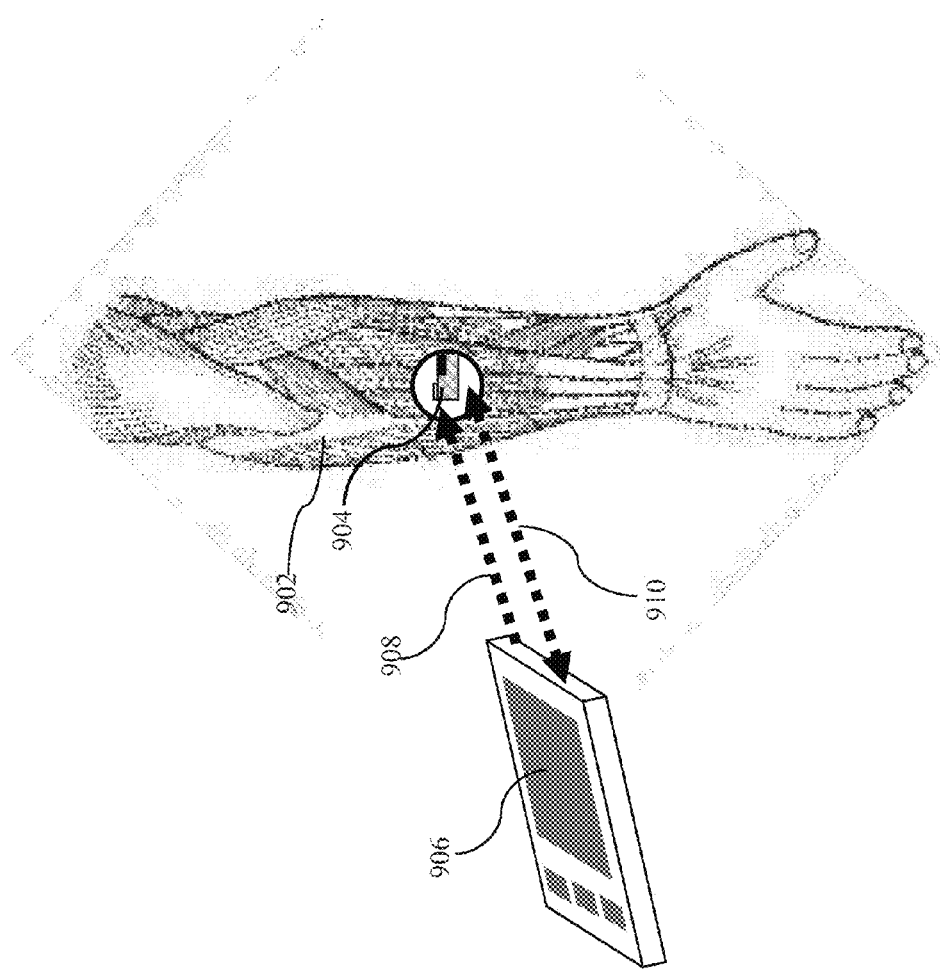
FIG. 9 shows an implantable transducer system, in accordance with an embodiment of the present disclosure.

FIG. 9 shows an example of an implantable transducer system. In this embodiment, an optically powered transducer (904) is implanted in an animal or human tissue (902). The optically powered transducer (904) is powered optically by an external reader (906). With sufficient power, the optically powered transducer (904) communicates with an external reader (906) wirelessly.

In accordance with an embodiment of the present disclosure, the optically powered transducer (904) may comprise the components of the transducer recited with reference to FIG. 1, including a photovoltaic collector, an electronic circuitry, and a sensor circuitry.

The optically powered transducer (904) remains inactive after its stored power is used up. To communicate with the optically powered transducer (904) (e.g., reading measurements), the reader (906) directs optical energy (908) at the optically powered transducer (904). The optically powered transducer (904) "wakes up" when light shines on it. As the transducer recited with reference to FIG. 1, the photovoltaic collector of the optically powered transducer (904) collects the optical energy (908) and powers up the electronic circuitry and the sensor circuitry of the optically powered transducer (904). The optically powered transducer (904) then communicates with the reader via a wireless data link (910), performs its designated operation (e.g. measuring blood sugar concentration via the sensor circuitry), transmitting measurement information, etc. When the optically powered transducer (904) finishes its operations or uses up its stored energy, it goes to an inactive or dormant state again. The wireless data link (910) comprises, for example, an optical data link. A person having ordinary skill in the art should understand that other wireless data links, such as Bluetooth® and WiFi, may be used.

Figure 10:
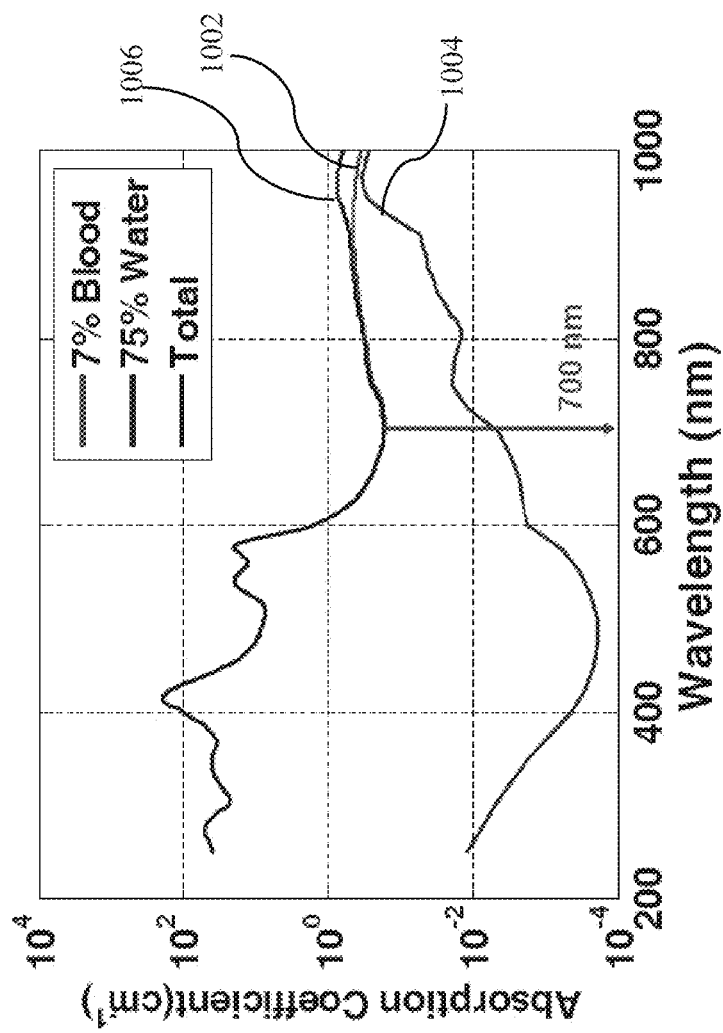
FIG. 10 shows wavelength-dependent absorption loss in blood and tissue.

In accordance with an embodiment of the present disclosure, the reader (906) generates optical energy with a near-IR semiconductor laser with a wavelength between 680 nm and 980 nm. FIG. 10 shows wavelength-dependent absorption loss in blood and tissue. The curve (1002) represents the absorption of 7% blood; the curve (1004) 75% water and the curve (1006) total. A low tissue absorption window starts around 700 nm. Thus, a near-IR semiconductor laser with a wavelength around 750 nm to 980 nm could efficiently provide optical energy through tissues up to several centimeters thick. In addition, near IR wavelengths may provide efficient photon-electron conversion and little heating on a silicon substrate. A person having ordinary skill in the art would understand the fabrication, design and use of a near-IR semiconductor laser. A person having ordinary skill in the art would also understand that the reader (1006) may use other light sources emitting wavelengths, e.g. from 800 to 1600 nm, such as around 850 nm and/or 980 nm. Also wavelengths around 1300 or 1500 nm can be used.

According to an embodiment of the present disclosure, the reader (906) may optically power and read many optically powered transducers at the same time and communicate each transducer with a specific laser wavelength or electronic signal signature The examples set forth above are provided to give those of ordinary skill in the art a complete disclosure and description of how to make and use the embodiments of the systems and methods for optically powering transducers and related transducers of the disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

We claim:

1. An optically powered transducer, comprising:
   a sensor circuitry adapted to convert an environmental or ambient signal of interest into a sensor electrical signal;
   an electronic circuitry adapted to process the sensor electrical signal;
   a multi-functional light source adapted to a) support an optical data communications link between the optically powered transducer and at least one another device, and b) provide light for performing optical spectroscopy; and
   a photovoltaic collector adapted to collect optical energy, convert the optical energy to electrical energy and power the sensor circuitry and the electronic circuitry with the electrical energy.

2. The optically powered transducer according to claim 1, wherein the optical data communications link is adapted to transmit a signal indicative of the environmental or ambient signal of interest.

3. The optically powered transducer according to claim 2, wherein the photovoltaic collector is further adapted to power the multi-functional light source with the electrical energy.

4. The optically powered transducer according to claim 2, wherein the multi-functional light source comprises a light-emitting diode or a semiconductor laser.

5. The optically powered transducer according to claim 2, wherein the multi-functional light source is adapted to emit light at a wavelength selected from around 850 nm, around 980 nm, around 1300 nm or around 1500 nm.

6. The optically powered transducer according to claim 1, further comprising at least one optical resonator adapted to increase absorption efficiency of the photovoltaic collector.

7. The optically powered transducer according to claim 6, wherein the at least one optical resonator comprises at least one resonant cavity.

8. The optically powered transducer according to claim 1, wherein the sensor circuitry is at least one of an implantable pressure sensor, a blood sugar detector, a medical implant, an autonomous sensor, a humidity sensor, a gas sensor, a pathogen sensor, a light sensor, a stress sensor, a strain sensor, or a motion sensor.

9. The optically powered transducer according to claim 1, wherein the electronic circuitry further comprises an energy storage apparatus adapted to store the electrical energy converted by the photovoltaic collector.

10. The optically powered transducer according to claim 1, wherein the electronic circuitry is further adapted to control operations of the optically powered transducer.

11. The optically powered transducer according to claim 1, wherein the electronic circuitry further comprises a circuit selected from a CMOS amplification circuit, a CMOS amplitude-to-pulse-width conversion circuit, or a CMOS laser driving circuit.

12. The optically powered transducer according to claim 1, wherein the sensor circuitry is operative as a blood sugar detector and wherein performing optical spectroscopy comprises at least one of refractive index, absorption or Raman measurements.

13. The optically powered transducer according to claim 1, wherein a first wavelength of the multi-functional light source is changed to a second wavelength when performing optical spectroscopy.

14. The optically powered transducer according to claim 1, wherein the multi-functional light source is a multi-wavelength light source for performing optical spectroscopy using multiple wavelengths.

15. A method comprising:
    powering an optically powered transducer by directing optical energy at the optically powered transducer;
    using a light source located in the optically powered transducer to enable an optical data link; and
    using the light source to provide light for performing optical spectroscopy.

16. The method according to claim 15, wherein the directing optical energy comprises providing optical energy of wavelength between around 800 nm and around 1600 nm.

17. The method according to claim 15, wherein using the light source to provide light for performing optical spectroscopy comprises changing a wavelength.

18. The method according to claim 15, wherein using the light source to enable the optical data link comprises using a first wavelength of light, and using the light source to provide light for performing optical spectroscopy comprises using a second wavelength.

* * * * *